US009592065B2

(12) United States Patent
Gregory

(10) Patent No.: US 9,592,065 B2
(45) Date of Patent: Mar. 14, 2017

(54) SHOULDER REPLACEMENT APPARATUS

(76) Inventor: Thomas Maurice Stewart Gregory, Paris (FR)

(*) Notice: Subject to any disclaimer, the term of this patent is extended or adjusted under 35 U.S.C. 154(b) by 599 days.

(21) Appl. No.: 13/635,634

(22) PCT Filed: Mar. 16, 2011

(86) PCT No.: PCT/GB2011/050521
§ 371 (c)(1),
(2), (4) Date: Sep. 18, 2012

(87) PCT Pub. No.: WO2011/114153
PCT Pub. Date: Sep. 22, 2011

(65) Prior Publication Data
US 2013/0023999 A1    Jan. 24, 2013

(30) Foreign Application Priority Data

Mar. 17, 2010  (EP) .................................... 10305265
Sep. 6, 2010   (GB) .................................. 1014694.2

(51) Int. Cl.
A61B 17/17   (2006.01)
A61B 17/88   (2006.01)
A61B 17/90   (2006.01)

(52) U.S. Cl.
CPC ...... A61B 17/1796 (2013.01); A61B 17/8897 (2013.01); A61B 2017/1778 (2013.01); A61B 2017/90 (2013.01); A61B 2090/062 (2016.02)

(58) Field of Classification Search
CPC . A61B 17/17; A61B 17/1717; A61B 17/1725; A61B 17/1735; A61B 17/1739–17/1796

USPC .................. 606/87, 96, 98, 103, 104, 80
See application file for complete search history.

(56) References Cited

U.S. PATENT DOCUMENTS

| 2,181,746 | A | * | 11/1939 | Siebrandt ............... A61B 17/17 408/115 R |
| 3,835,849 | A | | 9/1974 | McGuire |
| 4,312,337 | A | | 1/1982 | Donohue |
| D323,214 | S | | 1/1992 | Carchidi |
| 5,257,996 | A | | 11/1993 | McGuire |
| 5,833,611 | A | * | 11/1998 | Tepper ............... A61B 17/4241 600/462 |
| 6,099,547 | A | | 8/2000 | Gellman et al. |
| 8,257,359 | B2 | * | 9/2012 | Burkhart et al. ............... 606/87 |
| 2006/0074353 | A1 | | 4/2006 | Deffenbaugh et al. |

(Continued)

FOREIGN PATENT DOCUMENTS

CN    20082004535    1/2008
CN    20082052650    12/2008
(Continued)

OTHER PUBLICATIONS

Examination Report for European Application No. 11710553.6, mailed Jan. 16, 2015.
(Continued)

Primary Examiner — Christopher D Prone

(57) ABSTRACT

A surgical device for guiding a key wire during a shoulder arthroplasty procedure, including a guide for guiding a key wire during the process of drilling into a scapula, and a clamp configured to engage with the scapula neck such that a key wire located in the guide is located in a predetermined geometrical relationship with the scapula neck.

26 Claims, 17 Drawing Sheets

(56) References Cited

U.S. PATENT DOCUMENTS

2008/0154304 A1    6/2008  Crawford et al.

FOREIGN PATENT DOCUMENTS

| | | |
|---|---|---|
| CN | 20092019330 | 11/2009 |
| EP | 1 034 744 A1 | 9/2000 |
| EP | 1 082 943 A2 | 3/2001 |
| EP | 2135566 A1 | 12/2009 |
| RU | 2334478 | 9/2008 |
| WO | WO 2005/051209 A1 | 6/2005 |
| WO | WO 2006/001152 A3 | 2/2006 |
| WO | WO 2009/001109 A1 | 12/2008 |

OTHER PUBLICATIONS

Examination Report for EP Application No. 11710553.6, mailed Apr. 10, 2014.
International Search Report for International Application No. PCT/GB2011/050521, mailed Aug. 29, 2011.
Office Action for Japanese Application No. 2012-557610, mailed Oct. 21, 2014.
Office Action issued by Russian Patent Office corresponding to PCT/GB2011/050521, dated Feb. 10, 2015.

\* cited by examiner

SHOULDER REPLACEMENT APPARATUS

CROSS-REFERENCE TO RELATED APPLICATIONS

This application claims priority under 35 U.S.C. §371 to, and is a U.S. national phase application of, International Application No. PCT/GB2011/050521, filed Mar. 16, 2011, entitled "SHOULDER REPLACEMENT APPARATUS," which claims priority to European Application No. EP 10305265.0, filed Mar. 17, 2010 and Great Britain Application No. GB 1014694.2, filed Sep. 6, 2010, the disclosures of each of which are incorporated herein by reference in their entirety.

BACKGROUND

This invention relates to apparatus to facilitate the placement of shoulder prostheses, and in particular the placement of the glenoid part of shoulder any prostheses.

The replacement of damaged joints by prostheses is a well-established medical treatment to restore the function of a joint. In order to function correctly, and to provide the maximum lifetime for the prosthesis, it must be implanted in an optimum position. Placement in a non-optimal position may result in restricted movement of the joint, an increased rate of wear, and an increased rate of loosening of prostheses. Accurate placement of a prosthesis is therefore a critical part of the joint replacement process.

Partial, total Shoulder or reverse shoulder arthroplasty are effective treatments for damaged shoulder joints and in particular for shoulder arthritis. In a Total Shoulder Arthroplasty both the humeral and glenoid sides of the shoulder joint are replaced by prosthetic components. In a Partial Shoulder Arthroplasty only the humeral side is replaced. A reverse total shoulder arthroplasty, utilised in cases of associated rotator cuff deficiency, both sides of the joint are replaced, but a socket replaces the humeral head and a metaglenoid replaces the glenoid of the scapula.

There is general consensus that the success of total or partial shoulder arthroplasties is dependent on restoring the natural anatomy of the shoulder joint. Significant developments have been made with regard to the humeral side of shoulder prostheses, but recent observations have indicated that loosening rates for glenoid prostheses are very high and that glenoid loosening is the main complication after a total shoulder arthroplasty.

Implanting the glenoid component of a shoulder prosthesis in the optimum position is a difficult process due to, inter alia, limited bone stock of the native glenoid, poor understanding of the optimum position, and a lack of visible landmarks to assist in placement during surgery.

In a typical shoulder arthroplasty to replace the glenoid either supero-lateral or delto-pectoral approaches are made in the patient's outer, upper, arm. The humeral head is cut and the humerus is moved aside to provide a view of the glenoid surface. Only this surface, which is often deformed due to wear, is available as a guide to positioning the prosthetic glenoid and based on this limited information it is difficult for surgeons to accurately locate the optimum position.

Hence, the usefulness of the limited information is further degraded by erosion of the existing glenoid surface due to, for example, arthritis. In such circumstances the surgeon will place the glenoid prosthesis based on the visible surface as if it was in its original anatomical position. The surgeon is forced to estimate the original location based on pre-operative CT-scans, but without operative guidance assistance, this can lead to significant errors in position.

In reverse arthroplasty procedures the positioning of the metaglenoid is known to affect the rate of scapula notches in the resulting joint. Comparable considerations apply to reverse shoulder arthroplasty procedures as to conventional shoulder arthroplasty procedures.

The embodiments described below are not limited to implementations which solve any or all of the disadvantages discussed above.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

There is provided a surgical device for guiding a key wire during a shoulder arthroplasty procedure, comprising a guide for guiding a key wire during the process of drilling into a scapula, and clamp means configured to engage with the scapula neck such that a key wire located in the guide is located in a predetermined geometrical relationship with the scapula neck.

The predetermined geometrical relationship may provide a retroversion between a key wire guided by the guide and the scapula neck of approximately 2.1°.

The predetermined geometrical relationship may provide a retroversion between a key wire guided by the guide and the scapula neck in the range of 0.4° to 3.8°.

The predetermined geometrical relationship may provide a retroversion between a key wire guided by the guide and the scapula neck in the range of 0° to 5°.

The predetermined geometrical relationship may provide a superior inclination between a key wire guided by the guide and the scapula neck of approximately 1.9°.

The predetermined geometrical relationship may provide a superior inclination between a key wire guided by the guide and the scapula neck in the range of 0.3° to 3.5°.

The predetermined geometrical relationship may provide a superior inclination between a key wire guided by the guide and the scapula neck in the range of 0° to 5°.

The predetermined geometrical relationship may provide an offset between a key wire guided by the guide and the scapula neck of 0 mm.

The predetermined geometrical relationship may provide an offset between a key wire guided by the guide and the scapula neck in the range of −0.2 mm to 0.8 mm.

The predetermined geometrical relationship may provide an offset between a key wire guided by the guide and the scapula neck in the range of 0 mm to 1.5 mm.

The surgical device according may further comprise a second guide for guiding a key wire.

The surgical device according may comprise at least two parts detachably connected.

At least one guide may be adjustable to vary the predetermined geometrical relationship.

The grip portion may be shaped to engage with a scapula neck.

There is also provided a process of performing a shoulder arthroplasty comprising the steps of attaching a guide device to the neck of the scapula of the patient, wherein the guide device guides a key wire in a predetermined geometrical relationship relative to the scapula neck, drilling a key wire into the scapula utilising the guide device to guide the key wire; and implanting a replacement glenoid in an orientation defined at least in part by the key wire.

There is also provided a key wire for use in shoulder arthroplasty procedures comprising an expanded diameter portion and a measurement indicator, the measurement indicator providing an indication of distance along the axis of the key wire from the expanded diameter portion.

The expanded diameter portion may be located proximal to one end of the key wire and the measurement indicator extends along the key wire towards the end of the key wire distal from the expanded diameter portion.

The measurement indicator may comprise markings on the surface of the key wire.

There is also provided a kit comprising a surgical device and a key wire as described hereinbefore.

There is also provided a key wire for use in a shoulder arthroplasty procedures comprising a tip portion at a first end of the key wire comprising a pointed end, a body portion have a drill bit portion adjoining the tip portion and a measurement indicator, the measurement indicator extends along the key wire towards the end of the key distal from the tip portion, wherein the body portion has a larger diameter than the base of the tip portion.

The preferred features may be combined as appropriate, as would be apparent to a skilled person, and may be combined with any of the aspects of the invention.

BRIEF DESCRIPTION OF THE DRAWINGS

Embodiments of the invention will be described, by way of example, with reference to the following drawings, in which.

DETAILED DESCRIPTION

Embodiments of the present invention are described below by way of example only. These examples represent the best ways of putting the invention into practice that are currently known to the Applicant although they are not the only ways in which this could be achieved. The description sets forth the functions of the example and the sequence of steps for constructing and operating the example. However, the same or equivalent functions and sequences may be accomplished by different examples.

As noted previously, optimum performance of shoulder prostheses is obtained by replicating the natural anatomy of the shoulder joint. To achieve correct placement of the glenoid prosthesis a reliable indication of that placement is required. However, as discussed previously, such an indication is difficult to obtain due to the limited surgical opening utilised to place the glenoid prosthesis, and potential erosion of the natural glenoid surface.

Figure 1:
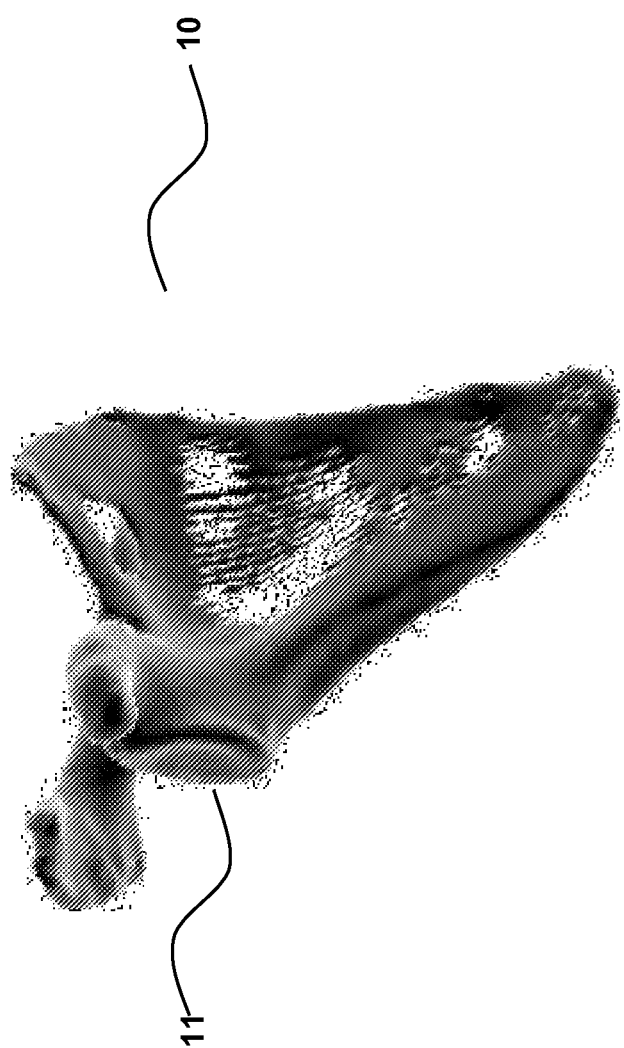
FIG. 1 shows a scapula bone.

FIG. 1 shows a diagram of the scapula bone 10 which includes the glenoid surface 11. The glenoid surface is located adjacent the scapula neck which leads to the main body of the scapula. A well-positioned prosthesis will replicate the anatomical position of the glenoid surface shown in this diagram. The dimensions of scapulas vary between people and therefore the precise dimensions and location of the glenoid surface may vary between patient and thus the correct location for a prosthesis must be determined on a case-by-case basis.

An analysis of scapula bone dimensions has been performed using 20 CT scans performed for reasons unrelated to shoulder problems.

Figure 2:
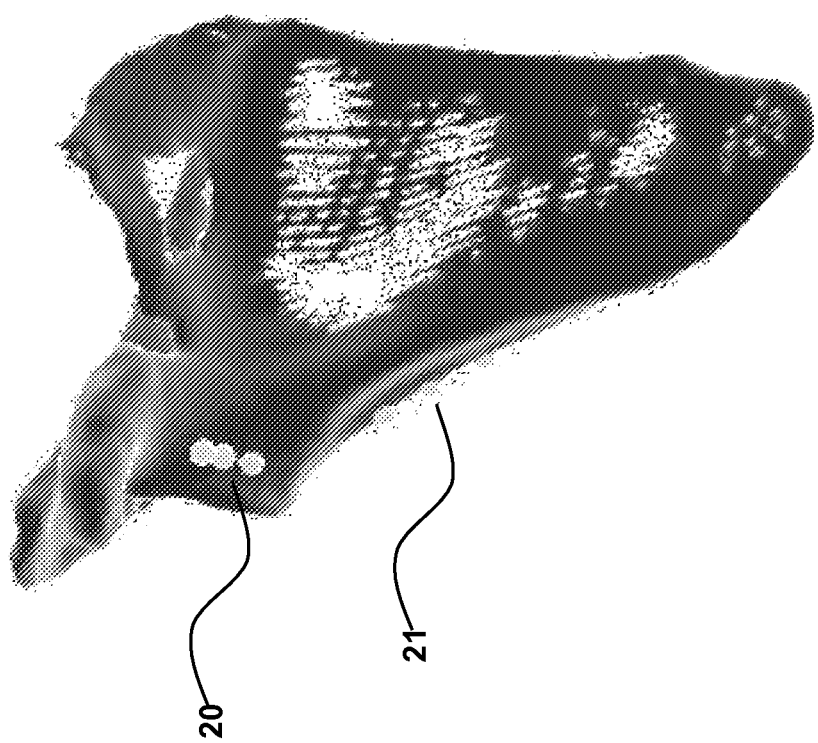
FIGS. 2, 3 and 4 show scapula bones with measurement locations marked.
Figure 3:
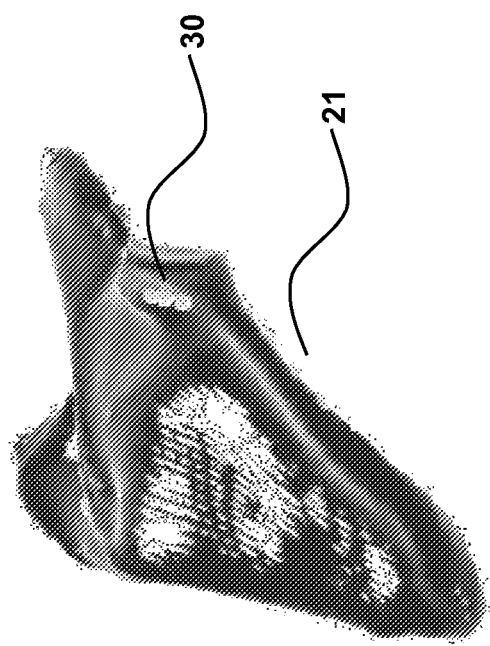
Figure 4:
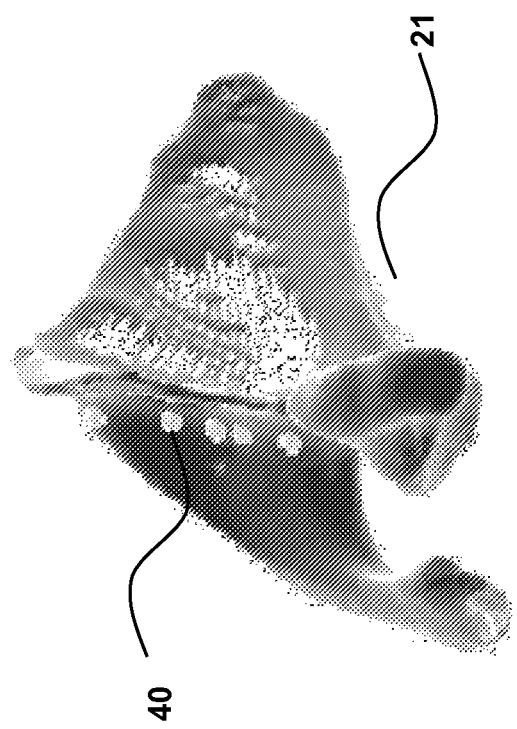

FIGS. 2, 3 and 4 show anterior, posterior and top views of a scapula obtained using a CT scan. Measurement points have been overlaid on to the image to define various planes for measurement and analysis. A glenoid plane is defined using points on the inferior ⅔ of the glenoid outer edge. A scapula neck plane is defined using points on the anterior 20 and posterior 30 of the scapula neck. A scapula blade plane is defined using points 21 along the lateral border of the scapula and the deepest part of the supraspinatus fossa 40.

In the following disclosure, the term 'perpendicular scapula blade' refers to a plane perpendicular to the actual, physical, scapula blade.

Glenoid Retroversion

Figure 5:
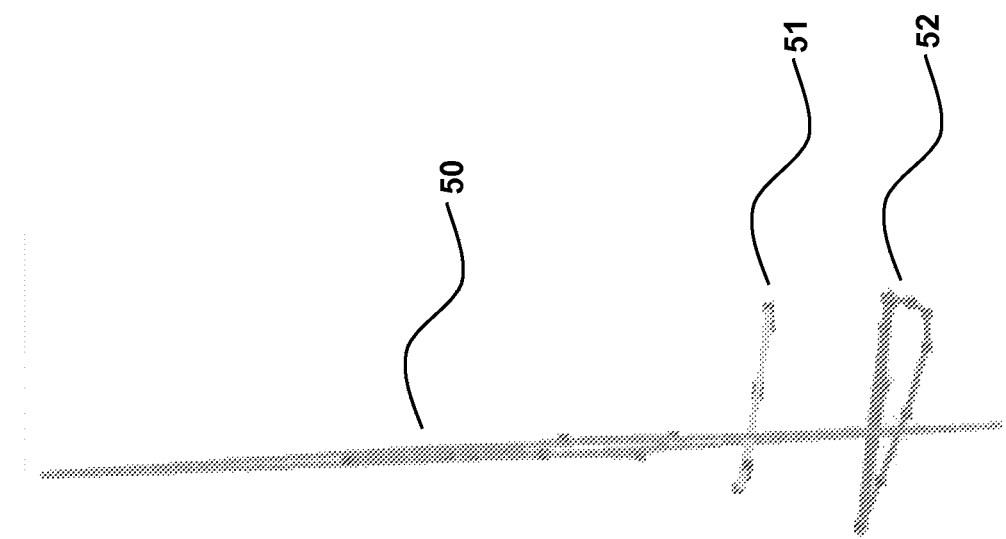
FIGS. 5, 6, 7, 8 and 9 show a models of the locations marked in FIGS. 2, 3, and 4 and the glenoid.

FIG. 5 shows a schematic representation of the scapula blade plane 50, the scapula neck plane 51 and the glenoid plane 52, when viewed from above. Table 1 shows the statistics of the glenoid retroversion seen in this view.

TABLE 1

|  | Glenoid/Perpendicular Scapula blade | Scapula neck/Perpendicular Scapula blade | Glenoid/ Scapula neck |
|---|---|---|---|
| Average (°) | 6.1 | 5.8 | 2.1 |
| SD | 3.4 | 4.2 | 1.7 |
| Min | −1 | 0 | 0 |
| Max | 13 | 13 | 5 |

Superior Inclination

Figure 6:
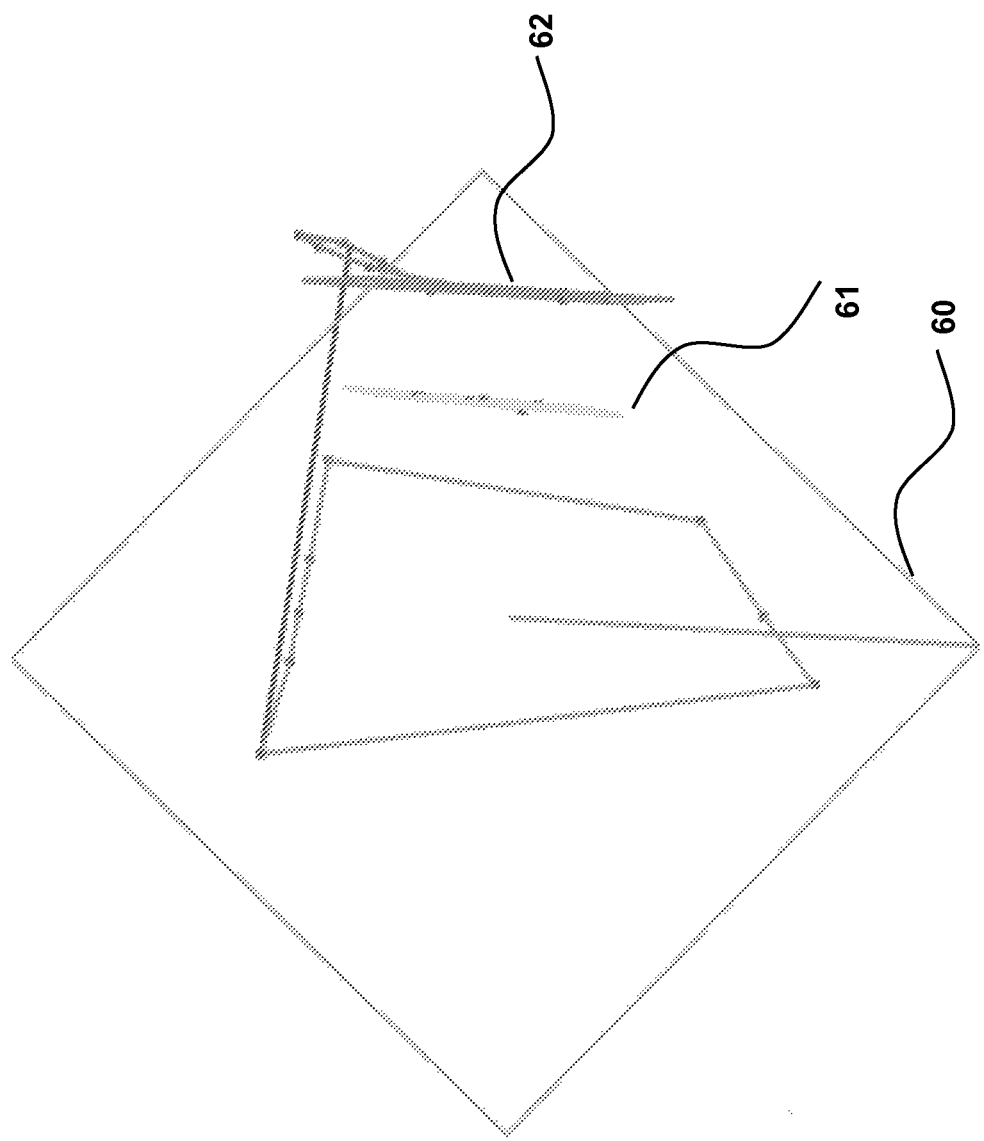

FIG. 6 shows a schematic representation of the scapula blade plane 60, the scapula neck plane 61 and the glenoid plane 62, when viewed from the anterior position. Table 1 shows the statistical values of the glenoid superior inclination seen in this view.

TABLE 2

|  | Glenoid/ Perpendicular Scapula blade | Scapula neck/ Perpendicular Scapula blade | Glenoid/Scapula neck |
|---|---|---|---|
| Average (°) | 12.05 | 11 | 1.9 |
| SD | 7.9 | 7.4 | 1.6 |
| Min | −4 | 0 | 0 |
| Max | 25 | 24 | 5 |

Rotation

Figure 7:
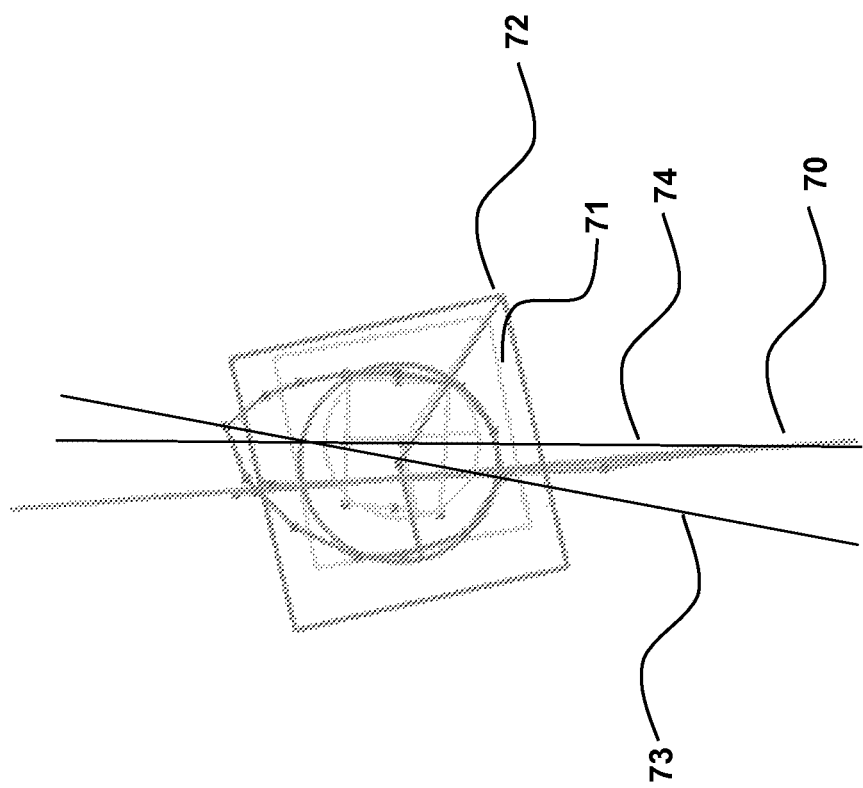

FIG. 7 shows a schematic representation of the scapula blade plane 70, the scapula neck plane 71 and the glenoid plane 72, when viewed from the outer lateral direction in a plane perpendicular to the scapula blade plane. Table 3 shows the statistical values of the glenoid rotation seen in this view.

TABLE 3

|  | Glenoid/Scapula blade plane | Scapula neck/Scapula blade plane | Glenoid/Scapula neck |
|---|---|---|---|
| Average (°) | 5.6 | 2.9 | 5.2 |
| SD | 4.3 | 2.7 | 1.1 |
| Min | 0 | 0 | 3 |
| Max | 15 | 10 | 7 |

The Glenoid/Scapula Blade angle is measured between the supero-inferior axis 73 of the glenoid (calculated using all points positioned around the outer edge of the glenoid) and the scapula blade plane. The Scapula neck/Scapula Blade is measured between the superio-inferior axis 74 located in the scapula neck plane 71 and centrally between the anterior and posterior points. The Glenoid/Scapula neck angle is measured between axis 73 and axis 74.

Glenoid Offset to Scapula Blade

Figure 8:
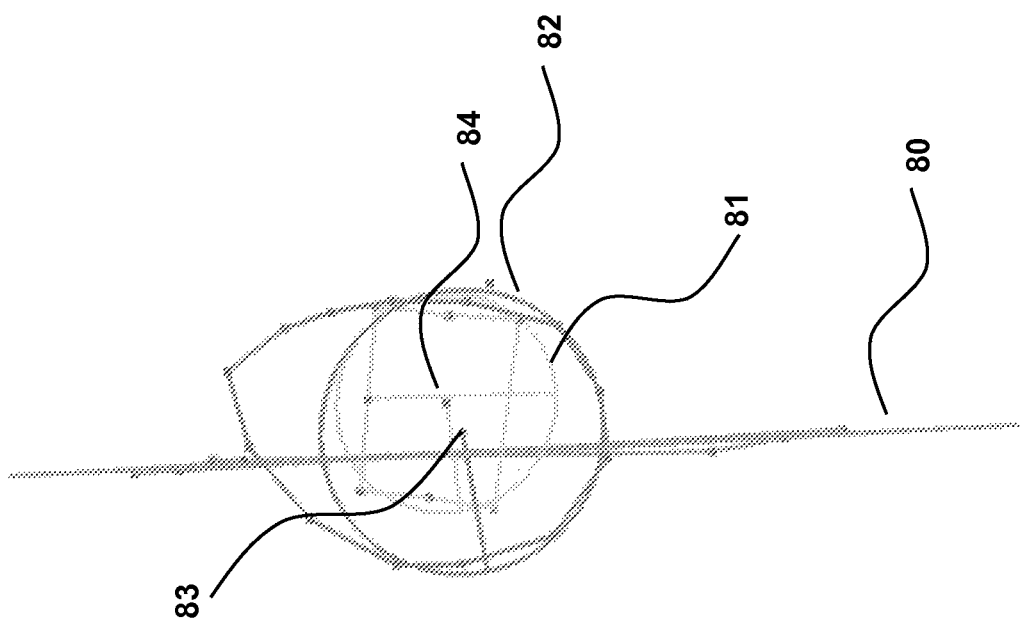

FIG. 8 shows a schematic representation of the scapula blade plane 80, the scapula neck plane 81 and the glenoid plane 82, when viewed from the outer lateral direction in the perpendicular scapula blade plane. Table 4 shows the statistical values of the offset position in this view.

TABLE 4

|  | Glenoid Centre/ Scapula blade plane | Centre Scapula neck/scapula blade plane |
|---|---|---|
| Average (mm) | 4.1 | 5.2 |
| SD | 1.8 | 1.2 |
| Min | 1.6 | 3.4 |
| Max | 8 | 8 |

The offset between the glenoid centre and the scapula blade plane is measured between the geometric centre 83 of the lower ⅔s of the points on the outer glenoid edge and the projection of this point on the scapula blade plane 80.

The offset between the Scapula neck and scapula blade plane is measured between the geometric centre 84 of the scapula neck points and the projection of this point on the scapula blade plane 80.

Glenoid Offset to Scapula Neck

Figure 9:
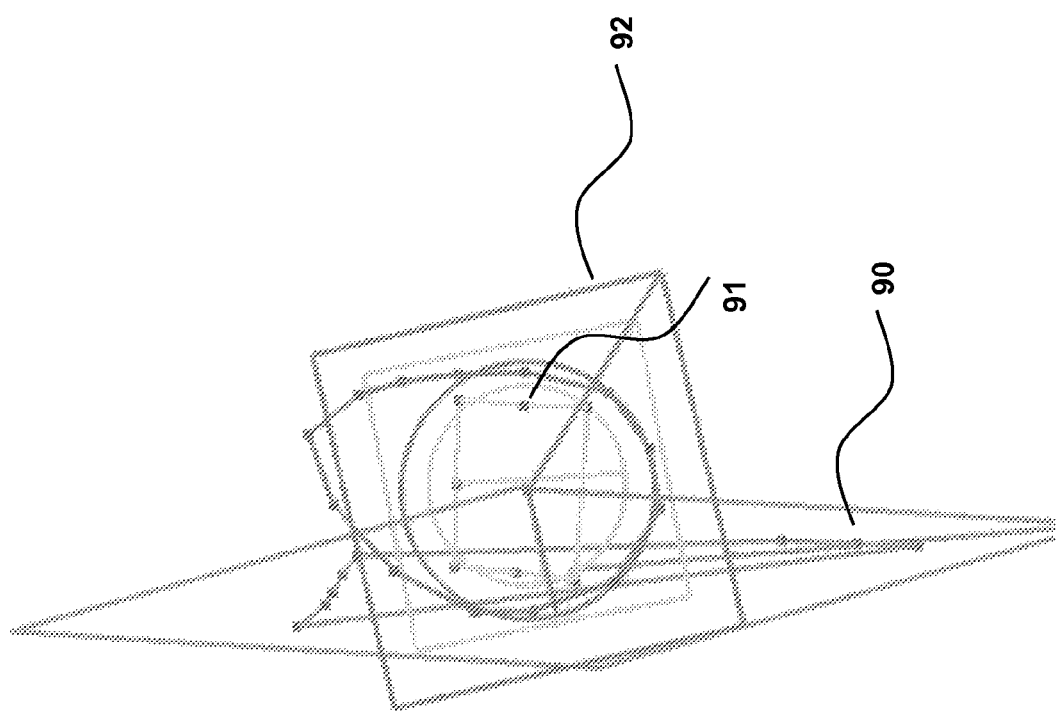

FIG. 9 shows a schematic representation of the scapula blade plane 90, the scapula neck plane 91 and the glenoid plane 92, when viewed from the outer lateral direction in the scapula neck plane. Table 5 shows the statistical values of the offset position in this view.

TABLE 5

|  | Centre of glenoid - centre of neck of scapula |
|---|---|
| Average (mm) | 0.3 |
| SD | 0.5 |
| Min | 0 |
| Max | 1.5 |

These measurements show that the anatomical glenoid position is closely related to the position of the measured locations on the scapula neck. The locations on the scapula neck can therefore be utilised as a guide for positioning a glenoid prosthesis in the anatomical position.

In relation to the scapula neck, the average position for the anatomically positioned glenoid is with a retroversion angle of 2.1° and a superior inclination of 1.9°. The glenoid is not circular and a rotation of 5.2° is the average rotation relative to the angle of the scapula neck.

Placement of a prosthetic glenoid in this position is therefore, on average, the optimum position. The data above also indicate that the range of positions is limited, providing evidence that the average position is not an extremely wrong position in any patient. For example, the average retroversion is 2.1° with a range of 0° to 5°. The maximum error by placement in the average position in any of the scapulas assessed would therefore be 2.9°. Measurements have indicated that current methods result in an average retroversion between the scapula blade plane and the glenoid of 5.76°, which is close to the anatomical average shown in Table 1 of 6.1°. However, the range of retroversion angles with current methods is −19° to 32°, with a standard deviation of 12.29°. The range shown in Table 1 is only −1° to 13°, with a standard deviation of 3.4°. This suggests significant errors in the placement of Glenoid prostheses using existing methods.

The above analysis shows that the centre of the glenoid and the centre of the scapula neck are aligned with an accuracy of 0.3+/−0.5 mm. Therefore, in case of spatial deterioration of the glenoid due to wear, the scapula neck locations provide a strong indication of the desired glenoid centre location.

Figure 10:
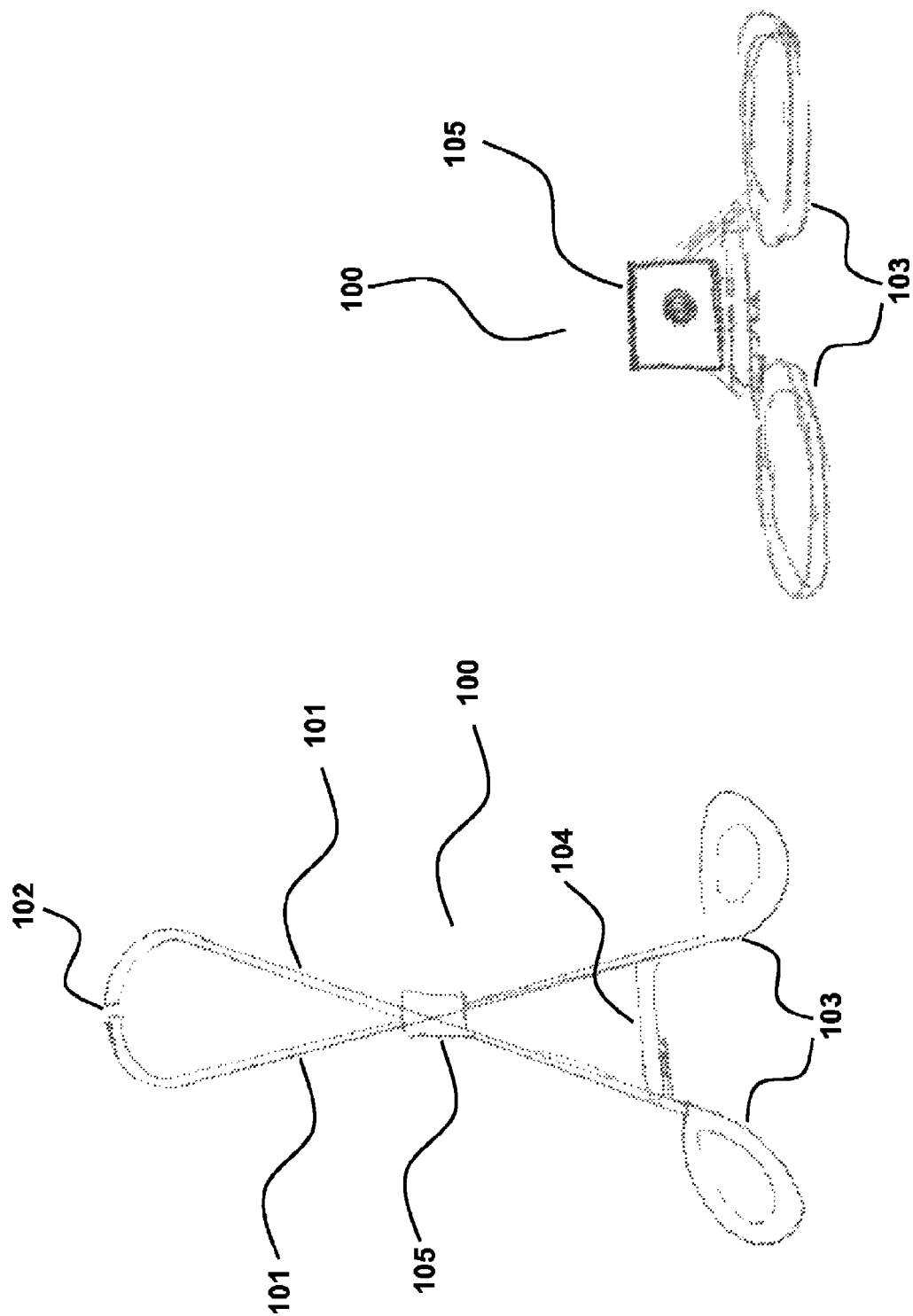
FIG. 10 shows a positioning tool.

FIG. 10 shows a schematic diagram of a tool 100 to assist in the placement of a glenoid shoulder prosthesis in the anatomical position. Arm portions 101 are hinged together to allow relative rotation between the two arms. One end of each arm 101 is terminated in a grip portion 102 and the other end in a handle portion 103. Latching means 104 are provided to latch the tool in a required position. A guide 105 for guiding a key wire is provided in a predetermined orientation relative to the grip portions 102.

The tool may be formed from any material with the required mechanical properties suitable for the construction of surgical instruments, for example metal.

The grip portions 102 may be shaped to improve stability of the tool when it is located on a scapula in the required location. For example, the grip portions 102 may be cylindrical with a diameter selected to match the expected location. Other shapes may be utilised as appropriate to engage with a scapula neck. The grip portions 102 may be detachable from the arm portions 101. The grip portions 102 may be formed in the same or different materials to the remainder of the tool. For example, polyethylene may be utilised for the grip portions, and metal for the other parts of the tool.

Figure 11:
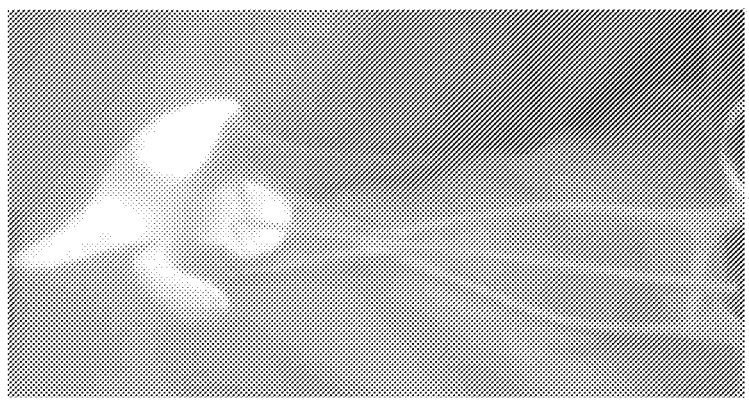
FIG. 11 shows a positioning tool located on a scapula.
Figure 11:
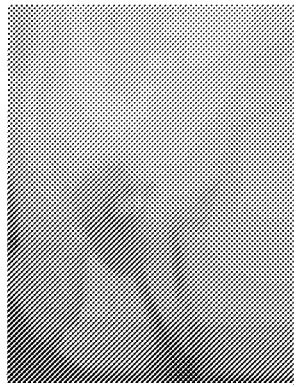
Figure 11:
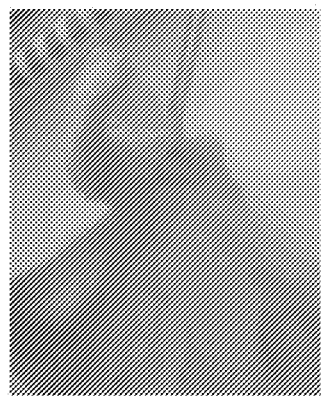

The grip portions 102 are configured to engage with the neck of a scapula in the position shown above. FIG. 11 show the tool in position on a scapula and with a key wire aligned with the axis of the tool demonstrating the correct alignment of that key wire. The predetermined orientation of the guide is selected according to the above data such that a key wire can be placed in a required position relative to the scapula neck. The key wire can thus be utilised to position a glenoid prosthesis in the required position relative to the scapula neck to recreate the anatomical glenoid position.

In a particular embodiment the guide provides a key wire orientation with a retroversion angle of 2.1° and a superior inclination of 1.9° relative to the scapula neck. As will be apparent to the reader, these angles are between the axis of the key wire and a plane perpendicular to the scapula neck plane. Although these are different to the planes and axis utilised above to analyse the anatomical retroversion, both have been shifted through 90° and therefore the values are consistent.

The guide is positioned along the axis of the tool and therefore the key wire offset to the centre scapula neck is zero. As per the above analysis this is extremely close to the anatomical offset which has an average value of 0.3 mm.

In other embodiments the orientation may vary. For example, the retroversion may lie in a range of 0.4° to 3.8°, or in a range from 0° to 5°, and the superior inclination may lie in the range from 0.3° to 3.5°, or in a range from 0° to 5°.

In other embodiments specific offsets may be provided other than zero in the embodiment described above. For example, the offset may lie in a range from −0.2 mm to 0.8 mm, or in a range from 0 mm to 1.5 mm.

The arms of the tool may be detachable to allow the tool to be positioned more easily. For example, the grip portions of each arm of the tool may be placed into position on the scapula and then joined to form the completed tool. Such a system reduces the space required around the glenoid to maneuver the tool into position. The detachable pivot may be constructed in any suitable manner, as will be apparent to the skilled reader. Furthermore, such a detachable tool may not require a pivot between the two arms, but other means of attachment between the arms to enable the tool to be secured to the scapula may be utilised. Such alternatives may also be applicable to tools without detachable arms.

The guide means for the key wire may be a hole through which the key wire may be passed, as shown in FIG. 10. The alignment of the hole guides the key wire to the correct location. Other forms of guide means will be apparent to the skilled person.

Some or all of the guide means may be adjustable to allow variation of the angles and offsets of the guides by the surgeon.

Figure 12:
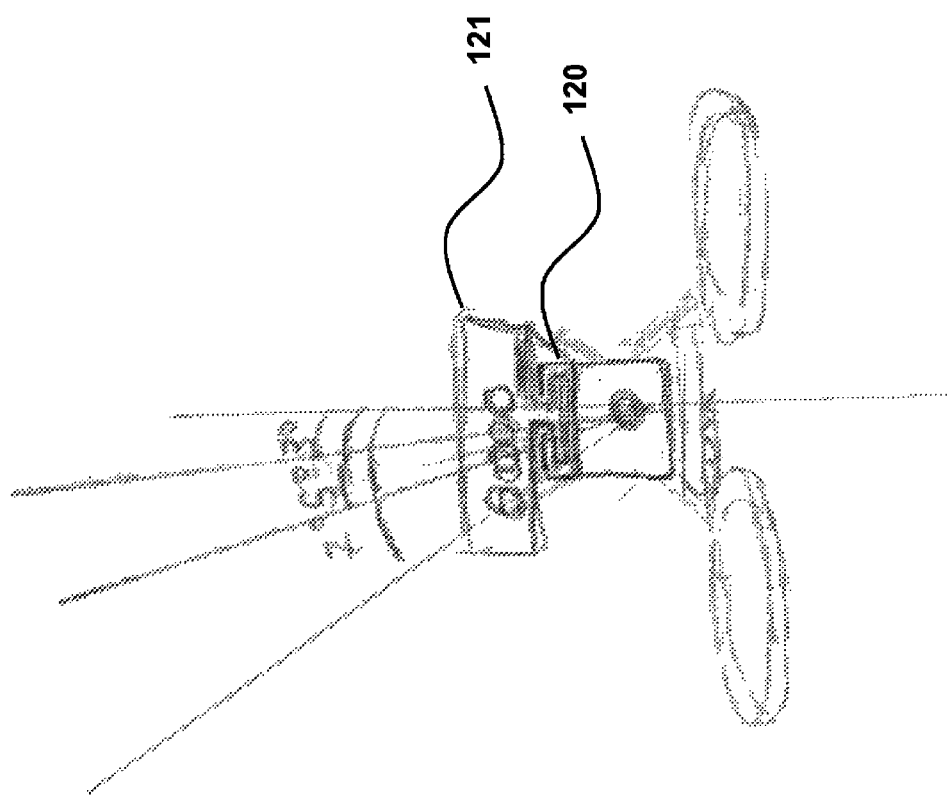
FIG. 12 shows a positioning tool with a second guide means attached.

It is common to insert two key wires to provide a rotational reference for cutting the prosthesis mounting into the scapula. As shown in FIG. 12, to facilities such placement the tool may be provided with an attachment point 120 for a second key wire guide 121. As shown in FIG. 12 a range of positions for the second key wire may be provided. The first guide is utilised to position the first key wire, and the required one of the second guides is selected to position the second key wire.

As demonstrated in the above analysis a rotation of 5.2° may be utilised to restore the average anatomical rotation of the glenoid. A second guide may therefore be provided to provide this angle between the two guide wires relative to the scapula neck. In other embodiments the angle may lie in the range of 4.1° to 6.3°, or in the range from 3° to 7°.

Where more than one second guide is provided, they are positioned at defined locations with respect to the first guide to allow tailoring of the tool to specific patients. Furthermore, one second guide, or set of second guides, may be provided for use on right scapulas, and one second guide, or set of second guides, for use on left scapulas, as the angles are mirrored for each side.

The use of two guide wires allows the rotation of the prosthetic glenoid to be set to a predetermined position. In a particular embodiment the second guide may be positioned to allow location of the glenoid with a rotation of 5.2° relative to the scapula neck. In other embodiments the rotation may be in the range 4.1° to 6.3°, or in the range from 3° to 7°. The relationship of the two key wires to achieve these angles will depend on the design of the prosthetic glenoid and the tools utilised to machine the scapula to accept the prosthesis.

A further component may be provided to attach to the two placed key wires to allow adjustment of the version of the glenoid attachment location.

The tool described hereinbefore is utilised in an operation as described below to implant a glenoid prosthesis during a shoulder arthroplasty procedure.

The initial stages of the operation to gain access to the glenoid are conducted as in conventional operations.

Once the existing glenoid is exposed, the guide tool is clamped onto the scapula with the grip portions located in the defined position on the scapula neck. As described previously, with the grip portion located in this position the tool, and hence guide part, is located in the predetermined orientation relative to the scapula neck and hence to the anatomical glenoid position.

Once positioned the guide is utilised to guide the positioning of a key-wire that will guide further steps; in particular the reaming of the glenoid and the drilling of hole(s) utilised to fix the glenoid implant to the scapula. Utilising the guide tool ensures the drilled key-wire is located in the centre of the scapula neck and is at the correct angle to penetrate within the centre of the scapula neck. This is achieved using the known orientation parameters as discussed above and according to which the guide tool is constructed. In prior art techniques where the drilling position is guided by the visible glenoid surface the angle of the key wire may be incorrect such that the drill approaches, or exits, the surface of the scapula bone.

In a particular embodiment the key wire is positioned with a retroversion angle of 2.1° and a superior inclination of 1.9° relative to the scapula neck. In other embodiments the orientation may vary. For example, the retroversion of the key wire may lie in a range of 0.4° to 3.8° or in a range from 0° to 5° relative to the scapula neck, and the superior inclination may lie in the range from 0.3° to 3.5° or in a range from 0° to 5° relative to the scapula neck.

In a particular embodiment the key wire is positioned along the centre of the scapula neck. In other embodiments the key wire may be positioned with an offset of 0.3 mm, or with an offset lying in the range from −0.2 mm to 0.8 mm, or in a range from 0 mm to 1.5 mm.

In a particular embodiment two key wires are inserted along an axis at an angle of 5.2° to the centre of the scapula neck. In other embodiments the angle may lie in the range of 4.1° to 6.3°, or in the range from 3° to 7°

Following positioning of the key wire the replacement may proceed according to conventional processes using the key wire position to drill the hole(s) for the implant fixation and to guide the shaping of the glenoid to accept the prosthesis and thereby ensure the correct positioning of the glenoid prosthesis with respect to the original anatomic position.

Figure 13:
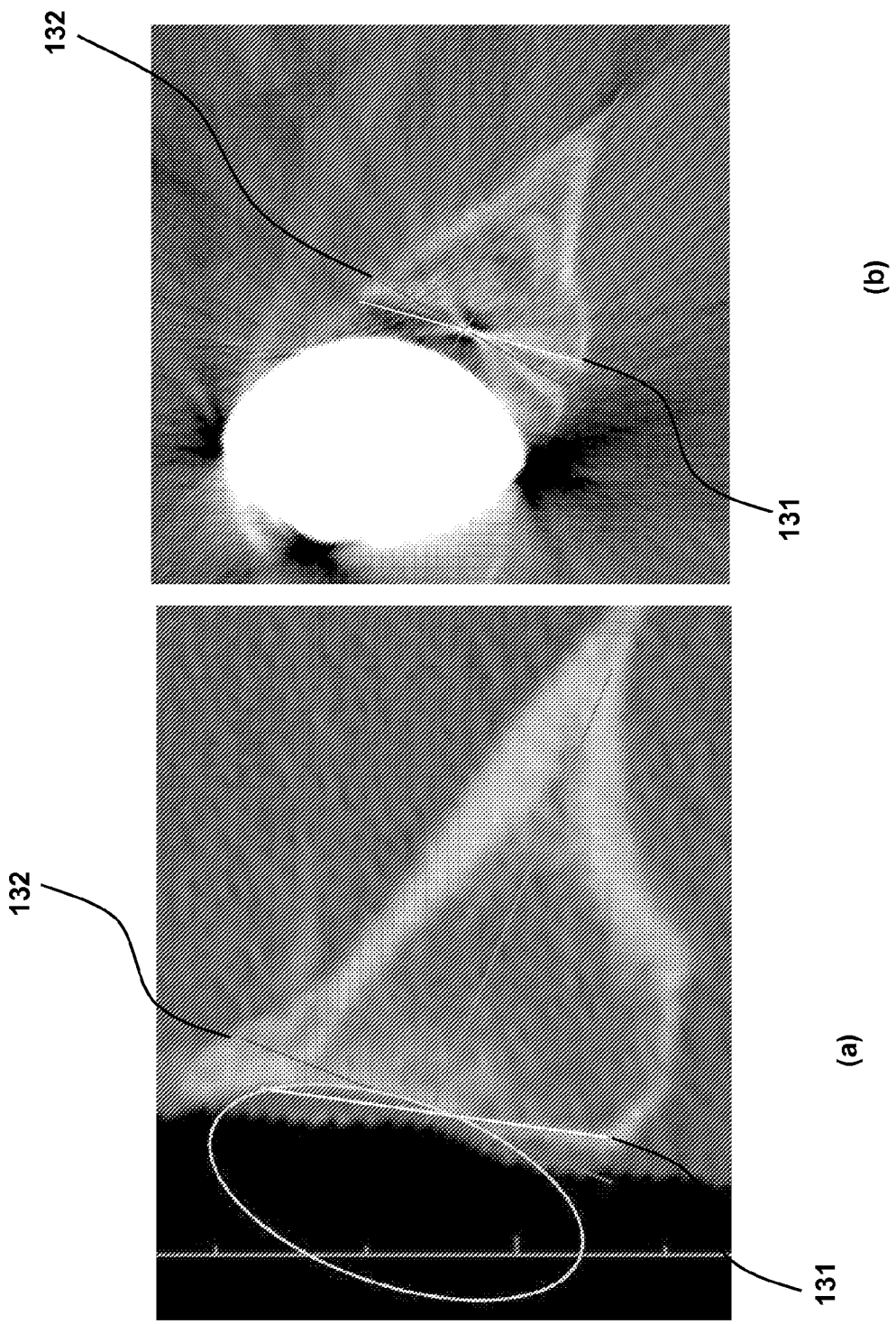
FIG. 13 shows a CT scan of a scapula before and after an arthroplasty procedure.

A guide tool constructed according to the statistical analysis described above was constructed an utilised in a shoulder arthroplasty. FIG. 13a shows an axial view of a CT scan prior to a shoulder arthroplasty procedure utilising the techniques described herein. Axis 130 marks surface of the glenoid which has suffered posterior wear. Axis 131 marks the surface of the anatomical glenoid position, calculated utilising the above techniques. The arthroplasty procedure was conducted utilising the technique and tools described above. As shown in FIG. 13b the prosthetic glenoid is positioned in accordance with the anatomical position indicating correct implementation and good alignment of the prosthesis. In prior art techniques the prosthesis would have been positioned in accordance with axis 130, resulting in significant errors in position and likely premature failure of the joint.

In the foregoing description the positioning of the glenoid is defined based on the statistical analysis set out above. In variations of the apparatus and techniques described herein the position may also or alternatively be defined based on pre-operative imaging of the patient. Such imaging may allow the positioning of the glenoid to more accurately match the particular shape of the patient's scapula. Pre-operative imaging may be utilised in conjunction with the above statistical data to provide an improved position based on the combined data. The tool described above may be provided with movable guides to allow adjustments based on pre-operative imaging.

Figure 14:
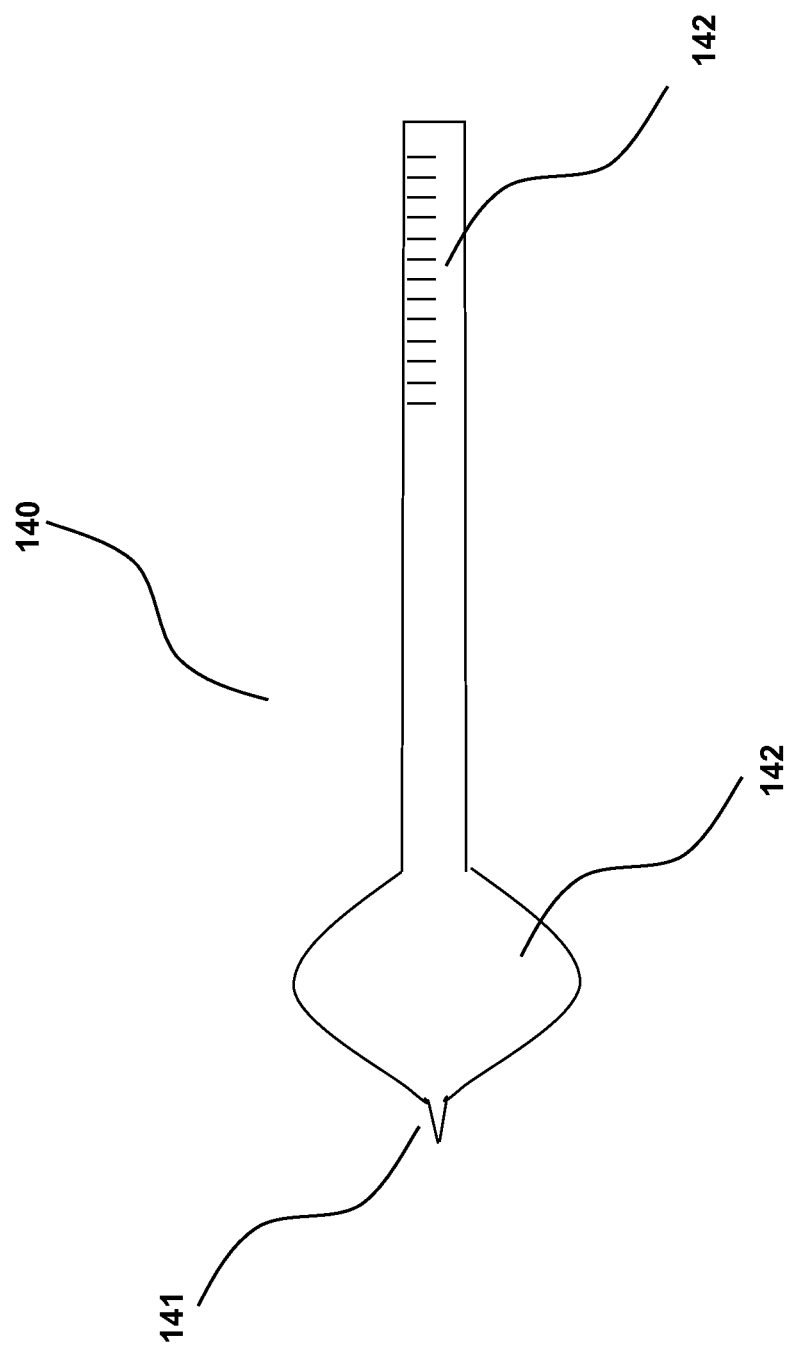
FIG. 14 shows a key wire for guiding lateral offset of a prosthesis.

FIG. 14 shows an apparatus to facilitate placing a glenoid prosthesis at the required lateral offset. The apparatus comprises a key wire 140 with a sharp end 141 and an enlarged diameter 142 at the base of the point A measurement scale 142 is provided along at least part of the length of the key wire to provide an indication of distance from the sharp end. FIG. 14 is not drawn to scale, but is greatly exaggerated in the vertical direction to clearly show the enlarged diameter region. The enlarged diameter region is not restricted to any particular form and may be located in other positions that directly at the base of the point.

FIG. 14 shows one possible example but any other shape suitable for insertion through a hole and retention therein may also be utilised. The measurement scale may be marked along the length of the key wire, for example by etched or printed markings, or any suitable means of indicating position.

Figure 15:
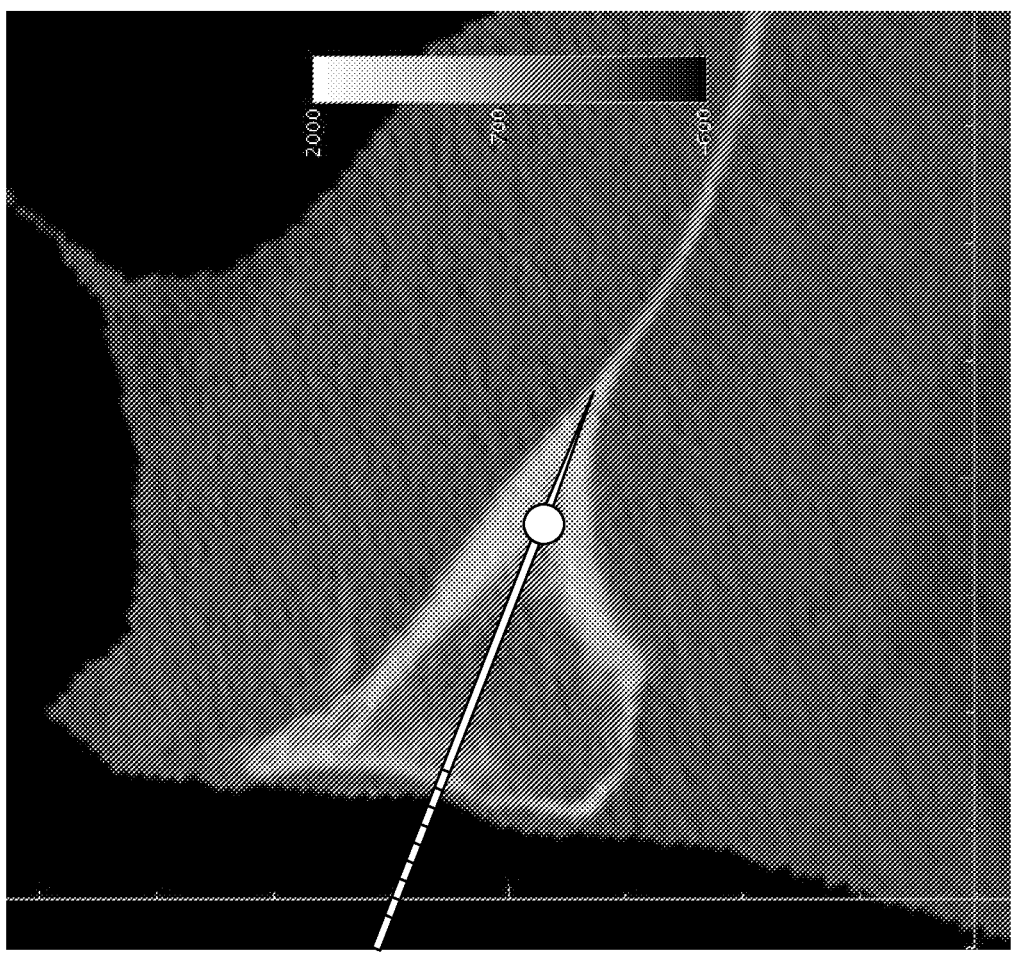
FIG. 15 shows a CT scan with the key wire of FIG. 13 overlaid.

The key wire of FIG. 14 is utilised in a two-step procedure for the placement of the key wire. A hole is drilled into the glenoid in the required orientation, for example as described previously using the guide tool described hereinbefore. The drill size is selected to accept the enlarged diameter region in frictional contact with the walls of the resulting hole. The hole is drilled to a depth at which resistance from the deep glenoid corticalis is felt though the drill. The key wire is then inserted into the hole, optionally utilising the guide tool. An initial resistance will be felt when the point enters the corticalis at the base of the hole, and then an increase in resistance will be felt with the expanded diameter region reaches the base of the hole at which point insertion is stopped. The measurement scale thus provides a known reference for placement of the prosthetic glenoid in respect of its lateral offset, and for optimising the component fixation depth and shape to the dimension of the glenoid, in order to increase the component fixation strength. FIG. 15 shows a CT scan overlaid with a schematic representation of the key wire of FIG. 14 showing an exemplary final location.

In an exemplary key wire, the enlarged diameter region of an exemplary 20/10e diameter key wire may have a diameter of 4 mm. A typical length is 20 cm.

Figure 16:
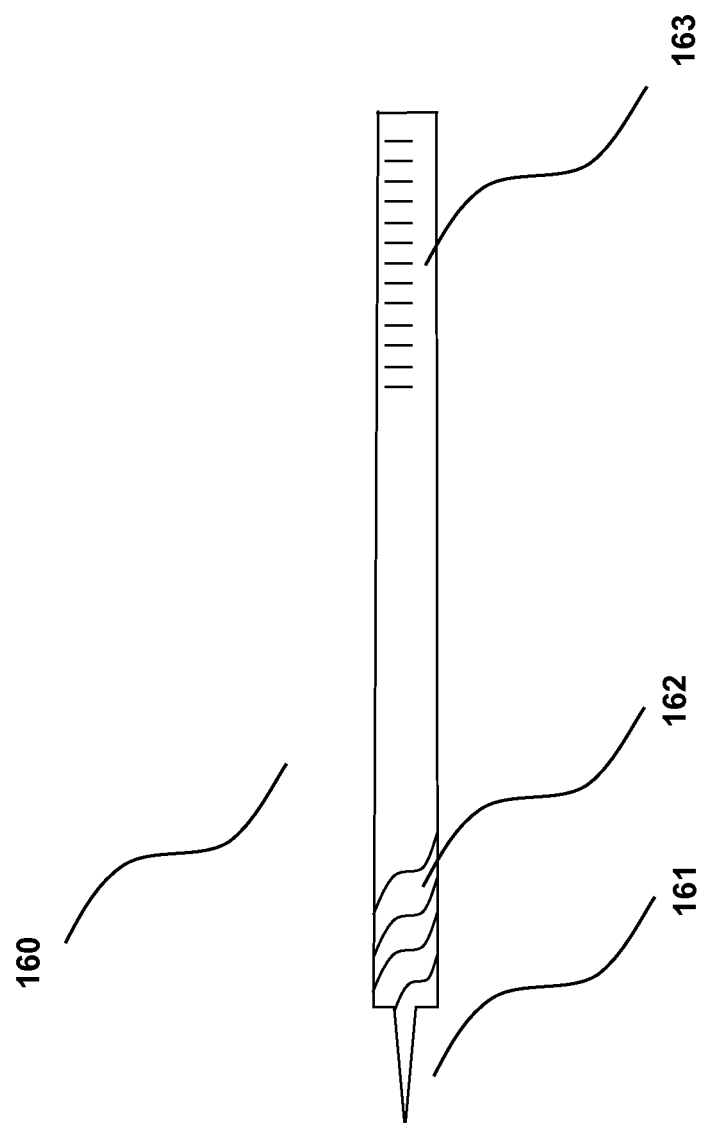
FIG. 16 shows a key wire for guiding lateral offset of a prosthesis.

FIG. 16 shows a combined drill and key wire 160 for guiding placement of a glenoid prosthesis. A first end of the key wire is provided with a point region 161 leading to a drill bit region 162 which has an enlarged diameter compared to the base of the point region. A measurement scale 163 is provided along at least part of the length of the key wire to provide an indication of distance from the first end.

Figure 17:
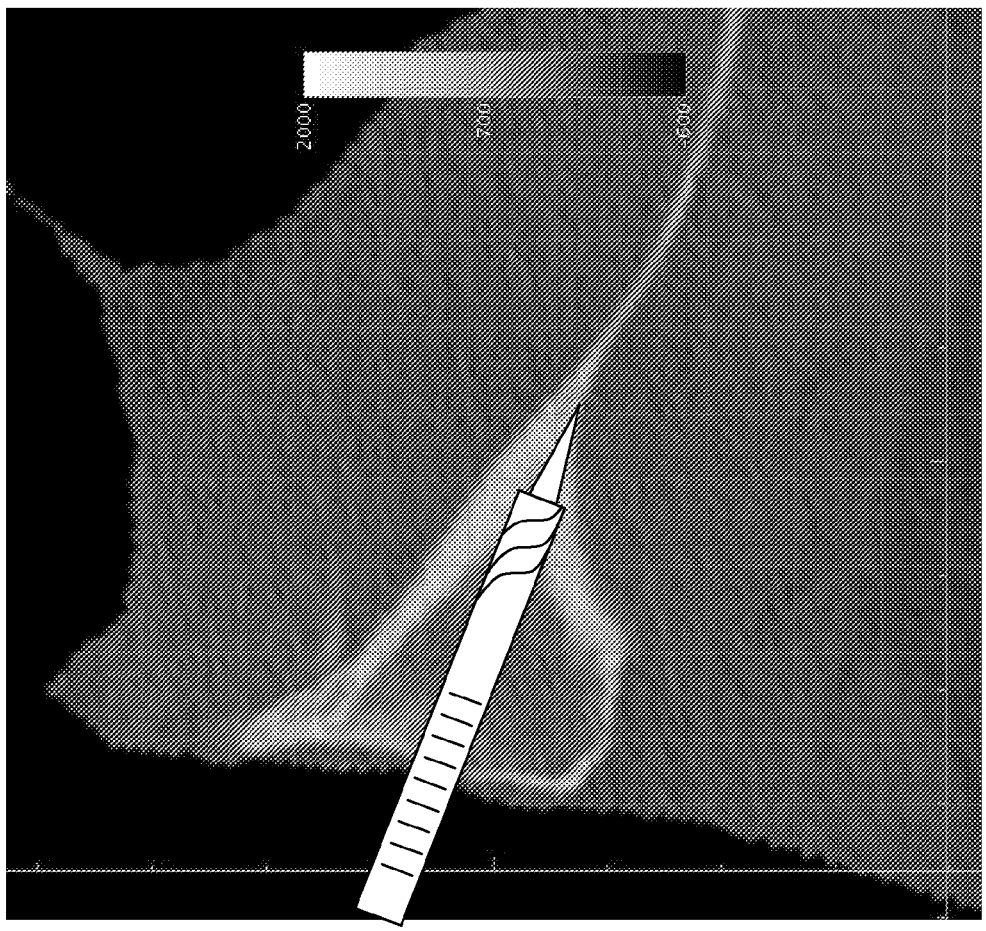
FIG. 17 shows a CT scan with the key wire of FIG. 16 overlaid.

In use a hole is drilled using the key wire of FIG. 16 and optionally utilising the guide tool described hereinbefore. An increased resistance will be felt as the point enters the deep corticalis of the glenoid and a subsequent increase in resistance will be felt when the enlarged diameter of the drill bit region enters the corticalis. Drilling is stopped when that second resistance is felt. The measurement scale then provides a known reference for placement of the prosthetic glenoid in respect of its lateral offset. FIG. 17 shows a CT scan overlaid with a schematic representation of the key wire of FIG. 16 showing an exemplary final location.

An exemplary key wire according to FIG. 16 may be utilise a 40/10 drill bit and key wire, with a 20/10$^e$ tip and having a total length of 20 cm.

Any range or device value given herein may be extended or altered without losing the effect sought as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages.

Any reference to an item refers to one or more of those items. The term 'comprising' is used herein to mean including the method blocks or elements identified, but that such blocks or elements do not comprise an exclusive list and a method or apparatus may contain additional blocks or elements.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought. The method blocks or elements identified do not comprise an exclusive list and a method or apparatus may contain additional blocks or elements.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the spirit or scope of this invention.

It will be understood that the benefits and advantages described above may relate to one embodiment or may relate to several embodiments. The embodiments are not limited to those that solve any or all of the stated problems or those that have any or all of the stated benefits and advantages.

The term 'comprising' is used herein to mean including.

The invention claimed is:

1. A surgical device for guiding a key wire for positioning of a glenoid prosthesis during a shoulder arthroplasty procedure, the surgical device comprising:
   a guide configured to guide the key wire during a process of drilling into a glenoid cavity and a neck of a scapula; and
   a pair of arms forming a clamp configured to clamp an anterior side and a posterior side of the neck of the scapula, each arm from the pair of arms terminating at a handle portion at a first end portion of the pair of arms and a grip portion at a second end portion of the pair of arms,
   with the pair of arms in a detached configuration, in which each arm from the pair of arms is physically separated from each other, and the grip portion of the first arm from the pair of arms engaged with the anterior side of the neck of the scapula and the grip portion of the second arm from the pair of arms engaged with the posterior side of the neck of the scapula, the pair of arms configured to be transitioned into an attached configuration, in which the first arm and the second arm are detachably hinged together to allow relative rotation between the pair of arms about a location at which the pair of arms are detachably hinged together, with the pair of arms in the attached configuration, both the grip portion of the first arm and the grip portion of the second arm are configured to engage with the neck of the scapula such that the key wire is disposed in a predetermined geometrical relationship with the neck of the scapula when the key wire is located within the guide, the predetermined geometrical relationship being defined such that the key wire positions the glenoid prosthesis in a predefined position relative to the neck of the scapula, the guide being aligned with an axis of the surgical device and collocated with the location at which the pair of arms are detachably hinged together such that the predetermined geometrical relationship provides an offset between the key wire guided by the guide and the scapula neck in the range of −0.2 mm to 0.8 mm when the pair of arms are in the attached configuration and the grip portion of the first arm is engaged with the anterior side of the neck of the scapula and the grip portion of the second arm is engaged with the posterior side of the neck of the scapula.

2. The surgical device according to claim 1, wherein the predetermined geometrical relationship provides a retroversion between the key wire guided by the guide and the neck of the scapula of approximately 2.1°.

3. The surgical device according to claim 1, wherein the predetermined geometrical relationship provides a retroversion between the key wire guided by the guide and the neck of the scapula in the range of 0.4° to 3.8°.

4. The surgical device according to claim 1, wherein the predetermined geometrical relationship provides a retroversion between the key wire guided by the guide and the neck of the scapula in the range of 0° to 5°.

5. The surgical device according to claim 1, wherein the predetermined geometrical relationship provides a superior inclination between the key wire guided by the guide and the neck of the scapula of approximately 1.9°.

6. The surgical device according to claim 1, wherein the predetermined geometrical relationship provides a superior inclination between the key wire guided by the guide and the neck of the scapula in the range of 0.3° to 3.5°.

7. The surgical device according to claim 1, wherein the predetermined geometrical relationship provides a superior inclination between the key wire guided by the guide and the neck of the scapula in the range of 0° to 5°.

8. The surgical device according to claim 1, wherein the predetermined geometrical relationship provides an offset between the key wire guided by the guide and the neck of the scapula of 0 mm.

9. The surgical device according to claim 1, further comprising a second guide configured to guide the key wire.

10. The surgical device according to claim 9, wherein the first guide defines a first guide axis therethough and the second guide defines a second guide axis therethough, the first guide axis being nonparallel to the second guide axis.

11. A surgical device according to claim 1, wherein the guide is adjustable to vary the predetermined geometrical relationship.

12. The surgical device according to claim 1, wherein the guide is adjustable relative to the pair of arms.

13. The surgical device according to claim 1, wherein the guide is disposed proximal to both the grip portion of the first arm and the grip portion of the second arm.

14. The surgical device according to claim 1, wherein the guide is (1) coupled to at least one arm from the pair of arms, and (2) disposed between both the grip portion of the first arm and the grip portion of the second arm, and both the handle portion of the first arm and the handle portion of the second arm.

15. The surgical device according to claim 1, wherein the guide defines an aperture configured to receive a portion of the key wire, the aperture defining a longitudinal axis therethough that is aligned to intersect the glenoid cavity when the pair of arms are clamped about the anterior side and the posterior side of the neck of the scapula.

16. A surgical kit comprising the surgical device according to claim 1 and the key wire, wherein the key wire includes an expanded diameter portion and a measurement indicator, the measurement indicator configured to provide an indication of a distance along an axis of the key wire from the expanded diameter portion.

17. A surgical device for guiding a key wire for positioning of a glenoid prosthesis during a shoulder arthroplasty procedure, the surgical device comprising:

a guide configured to guide the key wire during a process of drilling into a glenoid cavity and a neck of a scapula; and a pair of arms forming a clamp configured to clamp an anterior side and a posterior side of the neck of the scapula, each arm from the pair of arms terminating at a handle portion at a first end portion of the pair of arms and a grip portion at a second end portion of the pair of arms, with the pair of arms in a detached configuration, in which each arm from the pair of arms is physically separated from each other, and the grip portion of the first arm from the pair of arms engaged with the anterior side of the neck of the scapula and the grip portion of the second arm from the pair of arms engaged with the posterior side of the neck of the scapula, the pair of arms configured to be transitioned into an attached configuration, in which the first arm and the second arm are detachably hinged together to allow relative rotation between the pair of arms about a location at which the pair of arms are detachably hinged together, with the pair of arms in the attached configuration, both the grip portion of the first arm and the grip portion of the second arm are configured to engage with the neck of the scapula such that the key wire is disposed in a predetermined geometrical relationship with the neck of the scapula when the key wire is located within the guide, the predetermined geometrical relationship being defined such that the key wire positions the glenoid prosthesis in a predefined position relative to the neck of the scapula, the guide being collocated with the location at which the pair of arms are detachably hinged together when the pair of arms are in the attached configuration.

18. The surgical device according to claim 17, further comprising a second guide configured to guide the key wire.

19. The surgical device according to claim 17, further comprising a second guide configured to guide the key wire, the first guide defining a first guide axis therethough and the second guide defining a second guide axis therethough, the first guide axis being nonparallel to the second guide axis.

20. The surgical device according to claim 17, wherein the guide is adjustable relative to the pair of arms to vary the predetermined geometrical relationship.

21. The surgical device according to claim 17, wherein the guide defines an aperture configured to receive a portion of the key wire, the aperture defining a longitudinal axis therethough that is aligned to intersect the glenoid cavity when the pair of arms are clamped about the anterior side and the posterior side of the neck of the scapula.

22. A surgical device for guiding a key wire for positioning of a glenoid prosthesis during a shoulder arthroplasty procedure, the surgical device comprising:
a guide configured to guide the key wire during a process of drilling into a glenoid cavity and a neck of a scapula; and
a pair of arms hinged together to allow relative rotation between the pair of arms, the arms forming a clamp configured to clamp an anterior side and a posterior side of the neck of the scapula, each arm from the pair of arms terminating at a handle portion at a first end portion of the pair of arms and a grip portion at a second end portion of the pair of arms,
the grip portion of the first arm and the grip portion of the second arm are configured to engage with the neck of the scapula such that the key wire is disposed in a predetermined geometrical relationship with the neck of the scapula when the key wire is located within the guide, the predetermined geometrical relationship being defined such that the key wire positions the glenoid prosthesis in a predefined position relative to the neck of the scapula,
the guide being aligned with an axis of the surgical device and collocated with a location at which the pair of arms are hinged together such that the predetermined geometrical relationship provides an offset between the key wire guided by the guide and the scapula neck in the range of −0.2 mm to 0.8 mm when the grip portion of the first arm is engaged with the anterior side of the neck of the scapula and the grip portion of the second arm is engaged with the posterior side of the neck of the scapula.

23. The surgical device according to claim 22, wherein the predetermined geometrical relationship provides a retroversion between the key wire guided by the guide and the neck of the scapula of approximately 2.1°.

24. The surgical device according to claim 22, wherein the predetermined geometrical relationship provides a retroversion between the key wire guided by the guide and the neck of the scapula in the range of 0.4° to 3.8°.

25. The surgical device according to claim 22, wherein the predetermined geometrical relationship provides an offset between the key wire guided by the guide and the neck of the scapula of 0 mm.

26. The surgical device according to claim 22, further comprising a second guide configured to guide the key wire, the first guide defining a first guide axis therethough and the second guide defining a second guide axis therethough, the first guide axis being nonparallel to the second guide axis.

* * * * *